United States Patent
Sugiura et al.

(10) Patent No.: US 6,546,267 B1
(45) Date of Patent: Apr. 8, 2003

(54) BIOLOGICAL SENSOR

(75) Inventors: Keiichi Sugiura, Tokyo (JP); Toru Maeda, Tokyo (JP); Noriaki Todokoro, Tokyo (JP); Yoshinobu Nakae, Tokyo (JP); Teiji Ukawa, Tokyo (JP); Hideo Ozawa, Tokyo (JP)

(73) Assignee: Nihon Kohden Corporation, Tokyo (JP)

( * ) Notice: Subject to any disclaimer, the term of this patent is extended or adjusted under 35 U.S.C. 154(b) by 103 days.

(21) Appl. No.: 09/721,631

(22) Filed: Nov. 27, 2000

(30) Foreign Application Priority Data

Nov. 26, 1999 (JP) ............................................ 11-335551

(51) Int. Cl.⁷ ................................................ A61B 5/00
(52) U.S. Cl. ...................................... 600/310; 600/344
(58) Field of Search ................................ 600/310, 322, 600/323, 340, 344

(56) References Cited

U.S. PATENT DOCUMENTS

| | | | | |
|---|---|---|---|---|
| 3,647,299 A | * | 3/1972 | Lavallee | 250/208.3 |
| 3,998,550 A | * | 12/1976 | Konishi et al. | 356/39 |
| 4,805,623 A | * | 2/1989 | Jobsis | 250/339.12 |
| 4,830,014 A | | 5/1989 | Goodman et al. | 128/665 |
| 5,368,025 A | * | 11/1994 | Young et al. | 356/41 |
| 5,786,592 A | * | 7/1998 | Hok | 250/227.14 |
| 5,800,349 A | * | 9/1998 | Isaacson et al. | 600/323 |
| 5,810,724 A | * | 9/1998 | Gronvall | 600/310 |
| RE36,000 E | * | 12/1998 | Swedlow et al. | 128/633 |
| 5,891,021 A | * | 4/1999 | Dillon et al. | 600/310 |
| 5,957,840 A | * | 9/1999 | Terasawa et al. | 24/504 |
| 6,026,312 A | * | 2/2000 | Shemwell et al. | 600/310 |
| 6,047,201 A | * | 4/2000 | Jackson, III | 128/903 |
| 6,144,868 A | * | 11/2000 | Parker | 600/310 |

FOREIGN PATENT DOCUMENTS

| | | | | |
|---|---|---|---|---|
| JP | 53-26437 | 8/1978 | | A61B/5/00 |
| JP | 2-20252 | 5/1990 | | A61B/5/14 |

* cited by examiner

*Primary Examiner*—William C. Doerrler
(74) *Attorney, Agent, or Firm*—Sughrue Mion, PLLC

(57) ABSTRACT

A light emitting portion 3 and a light receiving portion 4 are separately formed, and firmly interposed between tape members 21 and 25 and between tape members 23 and 26, respectively. Those tape members are attached, by sticking, to the opposed locations of a surface of a finger 15 in a state that the optical axes of the light emitting portion 3 and the light receiving portion 4 are coincident with each other. The outer surfaces of them are covered with tape members 25 and 26, whereby the probe is attached to the finger 15.

18 Claims, 16 Drawing Sheets

BIOLOGICAL SENSOR

BACKGROUND OF INVENTION

1. Field of the Invention

The present invention relates to a biological sensor for non-invasively measuring a concentration of a material in a living body by the utilization of a plurality of lights having different wavelengths the light absorbing characteristics of which in the living body are different from one another. More particularly, the invention relates to a biological sensor which may easily be attached to the living body with high accuracy in measurement.

2. Related Art

The technique on the pulse oximeter is known for the technique for non-invasively and continuously measuring a concentration of a material in a living body by the utilization of different light absorbing characteristics of a plurality of wavelengths of lights. The measuring technique calculates an oxidation difference of hemoglobin in a blood of a living body by using a ratio of intensities of two wavelengths of lights whose light absorbing characteristics are different. It is known that the technique using a plurality of wavelengths of lights may also be available for calculating another material in the living body. An example of this is a technique to calculate a concentration of indo-cyanine green (ICG) in a blood by using three wavelengths of lights. A pulse oximeter using two wavelengths will be discussed, for explanation, in the description to follow. Also in the measurement using three or more wavelengths, however, the same thing is correspondingly applied to the basic technique, mainly the detection technique on the probe, a kind of biological sensors.

The pulse oximeter has rapidly been prevailed in the medical field in the world since the principle of the pulse oximeter disclosed in JP-B-53-26437. Presently, the pulse oximeter is one of the parameters indispensable for monitoring a condition of a patient, and it is a fairly general measuring item. The advantageous feature of the pulse oximeter resides in that it is able to measure an oxygen saturation in an arterial blood by a non-invasive measuring method.

The principle of the pulse oximeter is based on the fact that hemoglobin contained in the red blood cell in the blood changes its color when it is combined with oxygen, and hence, the arterial oxygen saturation can be obtained by measuring the light absorbing characteristic of the hemoglobin. Actually, one and the same sample being in the same state is measured by using two wavelengths of lights which are different in light absorbency, in the same condition. In this case, a ratio of the measurement results corresponds to the oxygen saturation in one-to-one correspondence. Lights having two wavelengths of about 660 nm and about 900 nm are used for the pulse oximeter measurement. A change of the light absorbancy of the light of 660 nm, caused by the oxygen saturation of the hemoglobin, is much larger than that of the light of 900 nm.

Specifically, as shown in FIG. 7, when a thickness D of a sample is changed by $\Delta D$ by a pulsation, and transmitted light I is attenuated by $\Delta I$, a change $\Delta A$ of the light absorbancy is given by $$\Delta A = \log[I/(I-\Delta I)] \approx EC\Delta D \quad (1)$$

Changes $\Delta A1$ and $\Delta A2$ of the light absorbancy (where 1 and 2 affixed to letters A indicate 660 nm and 900 nm) are measured and a ratio $\Phi$ of them is calculated, then we have $$\Phi = \Delta A1/\Delta A2 = E1/E2 \quad (2)$$

Thus, we have the light absorbancy ratio.

FIG. 8 shows in block and schematic form a basic construction of a pulse oximeter. A light source consists of two light emitting diodes (LEDs), and those LEDs alternately and rapidly flicker when receiving a signal from an oscillator (OSC). Light passes through a living tissue and reaches a photo diode (PD) which in turn converts an intensity of transmitted light into a corresponding current. The current is converted into a voltage, amplified, and split according to two wavelengths by a multiplexer (MPX). As a result, electric pulse signals of each wavelengths are obtained. Those pulse signals are logarithmically converted and the pulsating components of the signals are extracted through a band-pass filter (BPF). Each extracted one is a pulsating component $\Delta A$ of an attenuation of an object to be measured.

The pulsating component $\Delta A$ is defined by $$\Delta A = \log(Iout/I) \approx AC/DC \quad (3)$$

$$\Phi = \Delta A1/\Delta A2 \approx (AC1/DC1)/(AC2/DC2) \quad (4)$$

In the above expressions, AC and DC are, respectively, an amplitude of the pulsating component and a stationary component of the transmitted light. Thus, $\Phi$ as a ratio of the pulsating components of the lights of the two wavelengths can be obtained by using the division in place of the logarithmic process.

Finally, the oxygen saturation can be obtained by mathematically processing $\Phi$ or by using a conversion table for the $\Phi$.

To cause the computer to compute an exact oxygen saturation, the conditions required at the measuring location of the measured object through which the lights are transmitted may be concluded from the principle of the pulse oximeter such that "the lights having the wavelengths to be detected must be transmitted through the same location and travel an equal distance, and further must be influenced by the same living tissue and blood".

Let us consider the current measurement on the basis of the conditions required for the pulse oximeter "the lights having the wavelengths to be detected must be transmitted through the same location and travel an equal distance, and further must be influenced by the same living tissue and blood".

In an early stage of a probe for the pulse oximeter, an incandescent light bulb was used as a light source, and optical filters corresponding to the wavelengths were provided at two light receiving portions, whereby information on the two wavelengths was obtained. FIG. 9 shows an example of the early probe where an earlobe is used for an object to be measured.

In FIG. 9, an ear piece 2 forming an ear oximeter 1 is constructed with a light emitting portion 3 and a light receiving portion 4, which are optically coupled to each other, and a holder 6 including an appropriate slide which supports those elements and is able to adjust a distance between them and a fixing mechanism 5. A light emitting portion 3 contains a light source 7 therein, and a couple of photo transistors 8 and 9 are attached to the inside of the light receiving portion 4. The photo transistors 8 and 9 receives lights of wavelengths 660 nm and 900 nm, respectively. The ear piece 2 interposes an earlobe 12 with cushions 10 and 11 attached to the opposed surfaces of the light emitting portion 3 and the light receiving portion 4.

Thereafter, the LEDs are introduced into the probe, so that the probe size becomes small. This kind of probes as shown in FIGS. 10 and 11 have been used. The probe is attached to a finger, and the light emitting portion and the light receiving portion are provided in the upper and lower attaching portions of the probe. Those light emitting and receiving portions are oppositely disposed, and a tissue is interposed between them. Light transmitted through the tissue is detected. This type of the probe will be referred to as a "transmit type" of probe.

Another probe is shown in FIG. 12. As shown, a light emitting portion and a light receiving portion are secured onto a surface of a flexible member while being spaced a fixed distance (e.g., 10 mm). Lights scattered and reflected in the inner side of the fingertip or the like are measured. This type of the probe is referred to as a "reflection type" of probe.

The transmit type of the probe generally consists of a clip type of probe as shown in FIGS. 10 an 11, and a winding type of probe, which utilizes adhesion, as shown in FIGS. 13 and 14. FIG. 14 is a cross sectional view showing a structure of the FIG. 13 probe. In FIGS. 13 and 14, reference numeral 14 is a flexible tape member for holding the light emitting portion 3 and the light receiving portion 4 and to be applied to a finger 15. FIG. 17 shows an electric wiring between the light emitting portion 3 and the light receiving portion 4. For this type of the probe, a photo-electric sensor probe disclosed in JP-B-2-20252 is known.

The clip type of the probe is large in size. The light emitting portion and the light receiving portion are fixed while being confronted with each other. In the FIG. 10 probe, those portions are opened and closed by a hinge 16. Therefore, the optical axis of the probe is little shifted. In FIG. 11, those portions slide vertically, so that the probe is free from the shift of the optical axis.

This teaches that the light detection required for the pulse oximeter can be performed in an ideal condition. On the other hand, the winding type of the probe shown in FIGS. 13 and 14 has widely been spread in the form of "disposable use" in which cleaning and sterilizing of the probe are not required before and after the probe is attached to the object to be measured, in order to overcome the large size of the probe which is the disadvantage of the clip type of the probe and to reduce the cost to manufacture. Particularly, for the measurement of a neonate or a pediatric patient, the probe used must be small and clean. This also promotes such use of the probe.

The attaching of the conventional winding type of the probe shown in FIGS. 13 and 14 will be analyzed in detail.

FIGS. 15A to 15C diagrammatically show a probe when it is attached to fingers being different in size. In those figures, the light emitting portion 3, the light receiving portion 4 and a tape member 14 as a support structural member as an adhesive are illustrated in part. In each figure, the light emitting portion 3 was fixed to a lunula ungues of a nail bed of a finger 15, and the tape member was wound on the finger. If necessary, the light receiving portion 4 may first be fixed thereto. Since one and the same probe is used, a distance between the supports of the light emitting portion 3 and the light receiving portion 4 remains unchanged, as a matter of course. Accordingly, as seen, a position on the inner side of the finger tip portion to which the light receiving portion 4 is put is different finger by finger.

FIG. 16 shows the corrected attachment of the probe to the finger shown in FIG. 15A in which the tape member 14 is relatively long, which the correction is made such that the light emitting portion 3 and the light receiving portion 4 are oppositely disposed. The light emitting portion 3 and the light receiving portion 4 may be attached to locations that are oppositely disposed, but a sag is made by an extra sticking portion of the tape member. Actually, a wiring cable 16 of the light receiving portion 4 is contained in this portion as shown in FIGS. 17 and 18. This makes it impossible to remove this sag. When a patient moves, the patient rubs against the slack portion of the tape member to needlessly stimulate the patient. The needless stimulation will cause a rash of a weak skin of a neonate or a pediatric patient. FIG. 17 is an exploded view showing the probe, FIG. 18 is a perspective view showing the assembled one, and FIG. 19 is a sectional view showing the probe when it is attached to the finger 15. In those figures, reference numeral 17 is a cord which bundles a wiring cable 18 for supplying power source to the light emitting portion 3 and a wiring cable 16 for lading a signal out of the light receiving portion 4. Further, reference numeral 19 is a tape member for winding support structural members 13 and 14 around the finger and fixing them to the latter.

How a shift of a detecting position of the light, which is caused depending on a state of the attachment of the light emitting and receiving portions in the winding type of the probe, affects a measuring accuracy will be considered on "the component theoretically estimated as an error factor of the pulse oximeter" in light detected by the light receiving portion.

Firstly, "light not attenuated by blood", called "leak light", may be enumerated. An example of the leak light is LED light B or C leaking along the surface of a skin or into a space between the skin and the support structural member 14. The FIG. 16 case including a slack and the FIGS. 15(*a*) and 15(*c*) cases are the very typical examples in which the leak light relatively increases. According to the expression 4, the leak light is added as "light having no pulsation" that is the DC component of each wavelength.

$$\Phi = \Delta A1/\Delta A2 \approx (AC1/(DC1+R1))/(AC2/(DC2+R2)) \qquad (5)$$

In the above expression (5), R1 and R2 are leak light components.

These leak lights are not only transmitted through the blood per se but also is affected by reflection, absorption and the like by a skin tissue whose light absorption is different for each wavelength of light and on the tape surface. The leak lights, while varying in intensity, are added to the DC components as seen from the expression (5). As a result, the calculation result contains an error. For reference, an attenuation characteristic of fowl from which blood is removed, which is a representative example of a state of a tissue having no blood, is shown in FIG. 21. With regard to the light attenuation by the tissue where light is not attenuated by the blood, absorbing light A at 660 nm or therearound is apparently different from absorbing light B at 900 nm or therearound.

Another error cause is such that light scattering in the tissue changes depending on the wavelength of light, and hence a location in the tissue through which light has transmitted changes. A light intensity distribution changes depending on an angle with respect to the center of the light emitting element in each LED device. Where 0° is set at a position just above the surface of the light emitting element, an axis of light passes through 0° in both the longitudinal and cross sectional planes.

A light sensitivity of the light receiving element per se of the PD device also changes in value depending on the angle.

Also in this case, an axis of light, also called an optical axis passes through the position of 0° in both the longitudinal and cross sectional planes. It is safety to say that the optical axis is an axis providing substantially proper characteristics, although those are somewhat different by the lens effect of a transparent resin covering the element. Some examples of it are shown in FIGS. 22(a) and 22(b) in which dotted lines and solid lines indicate directivities of the light emitting element for different wavelengths. The light intensity difference described above is limited to the light intensity difference by an angle in a space. Actually, light, which is derived from a location of the living body to which the light is projected, is transmitted through the living tissue while at the same time is scattered by the tissue. In the case of the light projected through the surface of a skin, its scattering in the tissue changes depending on the wavelength. Accordingly, its distribution configuration is not uniform. As in an example of FIG. 23, a light distribution configuration varies depending on the wavelength of light. The longer the wavelength is, the harder the scattering of light is. IR light of 900 nm tends to be less scattered. Further, the scattering of light is caused by cells and cell membranes of blood cells and the like in the tissue. The scattering change dependent on the wavelength is more distinguished for a finger of a pediatric patient whose light transmitting thickness is thin. Accordingly, the intensities of lights having different wavelengths and the locations in the tissue through which the lights are transmitted are deviated depending on the location of the light receiving portion. This possibly causes an error in the light detection based on the measurement principle, and the error will lead to an error in the calculation.

As described above, in the measurement by the pulse oximeter, it is necessary to detect the lights transmitted through the same location and tissue and attenuated by the same living tissue and blood. The light receiving portion must detect lights of two wavelengths in the conditions which are equal to each other as much as possible. For this reason, it is desirable to transmit lights through the thickest location of the tissue and to align the light emitting and receiving portions with the optical axis as a position where the scattering of the light having one wavelength and that of the light having the other wavelength are both maximized. In a state as shown in FIG. 24 where the optical axis is shifted, the scattering of light in the tissue changes, so that light whose attenuation is deviated is detected, and there is a chance of increasing the leak light forming the error factor described already.

Those facts imply that in the measurement of a thin finger which is thin in thickness and tends to cause non uniform scattering of light, in particular the finger of a neonate or a pediatric patient, an exact coincidence of it with the optical axis is required. Further, in the finger of a neonate or a pediatric patient, a distance between the light emitting and receiving portions is shorter than that in the adult's one. The influence by the leak light is not negligible. Accordingly, it is implied that an error of the measurement, which is influenced by a shift of the optical axis, will increase. The reflection type of the probe is a typical example of the probes suffering from the great optical axis shift. This type of the probe is disadvantageous in securing exactness in measurement, although it has an advantage of easy attachment.

The winding type of the probes in which the distance between the light emitting and receiving portions is set to two kinds are currently marketed in the light of production cost in manufacturers and the inventory management in actual hospitals. etc. An operator can select the probe suitable for the patient from his experience to certain degree. However, the probe will be not always fit to the patient since the distance between the light emitting and receiving portions is fixed in value. Accordingly, erroneous measured values will be produced highly possibly. In other words, we recognized such a structural problem of the disposable type probe, which can be manufactured at low production cost, that the light emitting portion and the light receiving portion are fixed to one and the same tape (support structural member).

When a conventional probe in which the light emitting and receiving portions are assembled into a unit form as shown in FIG. 18 is attached to a person to be measured by use of a long strip-like tape member 19, care must be taken so as not to mistakenly attach the probe to an incorrect location of the measured person. Further, there is the possibility that the long tapes 19 incorrectly adhere to one another. To avoid this, the operator must carefully apply the probe to the measured person. Particularly when the patient is not cooperative to attach the probe, when the tape is passed through between a target finger and another finger, it is frequently attached to another finger. Generally, as the attaching and detaching of the tape of the probe are repeated, an adhesive force of the probe tape becomes weaker. Accordingly, when the tape is attached to an incorrect location of the patient, the probe fails to exhibit its own performance.

Where the light emitting portion 3 and the light receiving portion 4 are interposed between the tape members 13 and 14, holes 14a and 14b as light transmission windows are formed in the tape member 14 to be applied to a location to be measured. Those windows allow a sufficient amount of light to pass therethrough for reception and transmission. With provision of the holes 14a and 14b, a step is formed between the hole 14a and its peripheral part by a height of the tape member 14, as shown in FIG. 25 showing a portion including the light emitting portion 3 in cross section. This step will create a partial insertion 15a of the tissue at the probe attaching location. As a result, ischemia or stasis will occur at a contour of the tissue along the edge of the hole, i.e., a circumferential edge 15b.

It is readily understood that transmission of light through such a location of the tissue as to receive a physical stress from exterior should be avoided in order to secure an accurate measurement of a patient's condition. A thin transparent member, such as nonwoven fabric may be interposed between the holes 14a, 14b as the light transmission windows and the skin at the probe attaching location. In this case, the member, together with the skin, is often put into the hole because of its flexure.

An approach to remove the steps by filling the holes 14a and 14b with transparent material, e.g., resin, is disadvantageous in complexity of the manufacturing process, long time taken for the manufacturing, and hence poor manufacturing efficiency. Further, unless the elastic characteristic of the material is exactly the same as that of the tape members 13 and 14 around the material, its edge portions corresponding to the boundaries between it and the holes 14a and 14b form a step. Specifically, if an elasticity of the filling material is stronger than that of the tape member around it, the whole filling portion is pressed against the skin. If the elasticity of the filling material is weaker than that of the tape member around it, a partial insertion of the skin is caused.

SUMMARY OF INVENTION

The present invention has been made in view of the above circumstances, and has an object of providing a biological sensor which is easy to be attached and has a high measuring accuracy.

According to the present invention, there is provided a biological sensor for non-invasively measuring a concentration of a material in a living body by detachably attaching the biological sensor to a skin surface of the living body, the biological sensor having a light emitting portion and a light receiving portion for detecting lights which is emitted from the light emitting portion and transmitted through the living body, wherein the light emitting portion and the light receiving portion may be attached to the opposed locations of a skin surface of the living body, and the light emitting portion and the light receiving portion are firmly fixed to separate support structural members, respectively.

In the biological sensor, the support structural members include pairs of tape members which interpose the light emitting portion and the light receiving portion, and the tape members covering a light emitting surface of the light emitting portion and a light receiving surface of the light receiving portion are transparent.

In the biological sensor, at least one of the support structural members is symmetrically configured with respect to a line on which the light emitting portion or the light receiving portion lies.

In the biological sensor, at least one of the support structural members is symmetrically configured with respect to a line on which the light emitting portion or the light receiving portion lies, and the support structural member includes wing portions extending to both sides.

In the biological sensor, the support structural members are each symmetrically configured with respect to a line on which the light emitting portion or the light receiving portion lies respectively and the support structural members each include wing portions extending to both sides.

In the biological sensor, at least one of the support structural members is furnished with a mark being oriented in a direction in which the support structural member is attached to the living body location.

In the biological sensor, the light emitting portion and the light receiving portion are separately formed. Accordingly, those may easily be attached to a skin surface of a living body in a state that their optical axes are coincident with each other. As a result, a concentration of a material in a living body may accurately be measured. In the biological sensor, the tape members to be brought into contact with the patient's skin are transparent. With this feature, there is no need of the light transmission holes, which are formed at the measuring locations of the conventional tape members. In this respect, a seamless structure is realized. Accordingly, when the biological sensor is fit to the patient for a long time, the patient's skin is not damaged and the invasion to the skin is minimized.

In the biological sensor, the support structural member or members are each symmetrically configured with respect to a line on which the light emitting portion or the light receiving portion lies. Further, in the biological sensor, one of the support structural members is furnished with a mark and both of the support structural members are each furnished with a reference line being oriented in a direction in which the support structural member is attached to the living body location. Therefore, the support structural members may easily be attached to correct locations of a living body. The furnished mark also indicates that the biological sensor is used for one of a neonate or a pediatric patient. The furnished reference line is referred to when the light emitting portion and the light receiving portion are attached in a state that the optical axes of the light emitting portion and the light receiving portion are coincident with each other.

DETAILED DESCRIPTION OF PREFERRED EMBODIMENTS

Figure 1:
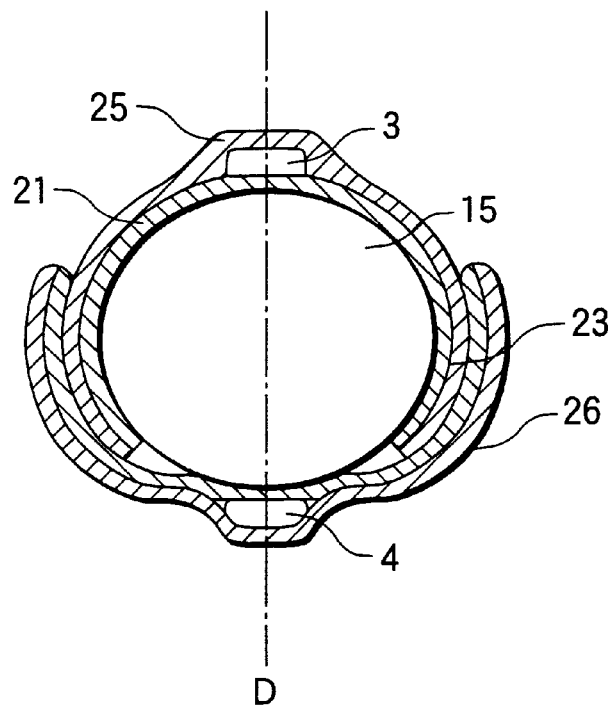
FIG. 1 is a cross sectional view showing a biological sensor which is an embodiment of the invention.
Figure 2:
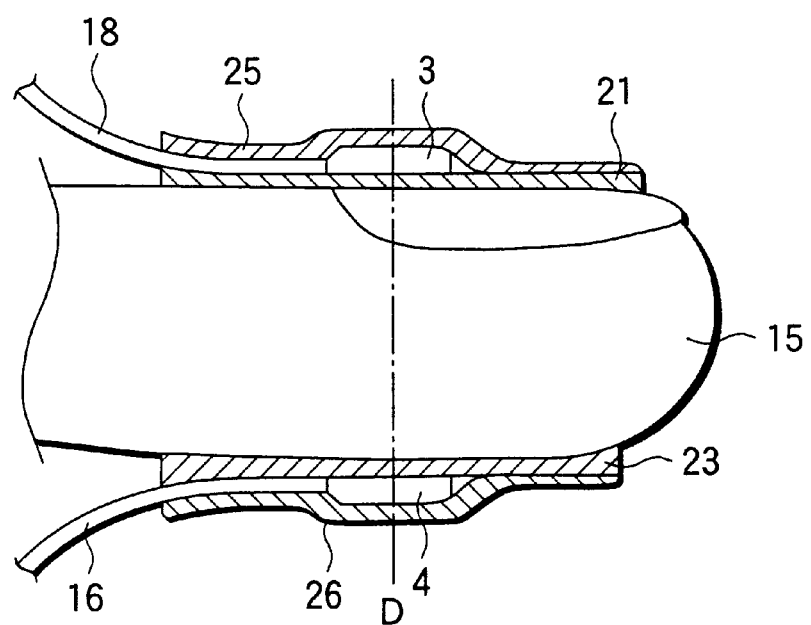
FIG. 2 is a longitudinal sectional view showing the FIG. 1 sensor.
Figure 3A:
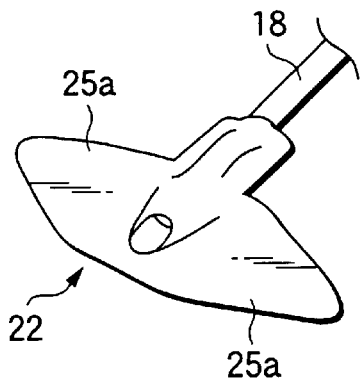
FIGS. 3(a) to (d) are perspective views showing external appearances of light emitting portions and light receiving portions shown in FIGS. 1 and 2 before those are attached.
Figure 3B:
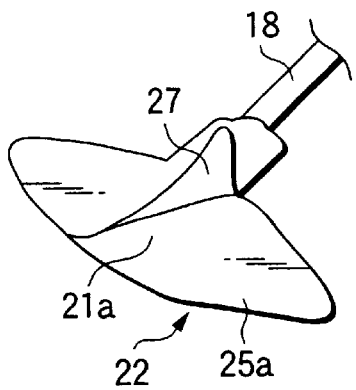
Figure 3C:
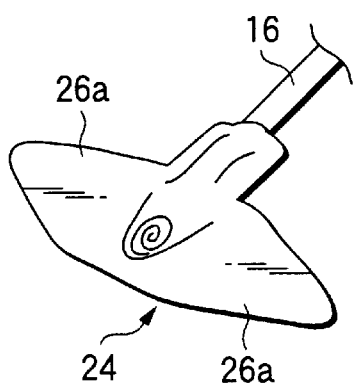
Figure 3D:
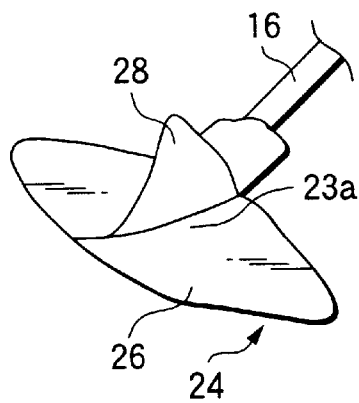
Figure 11:
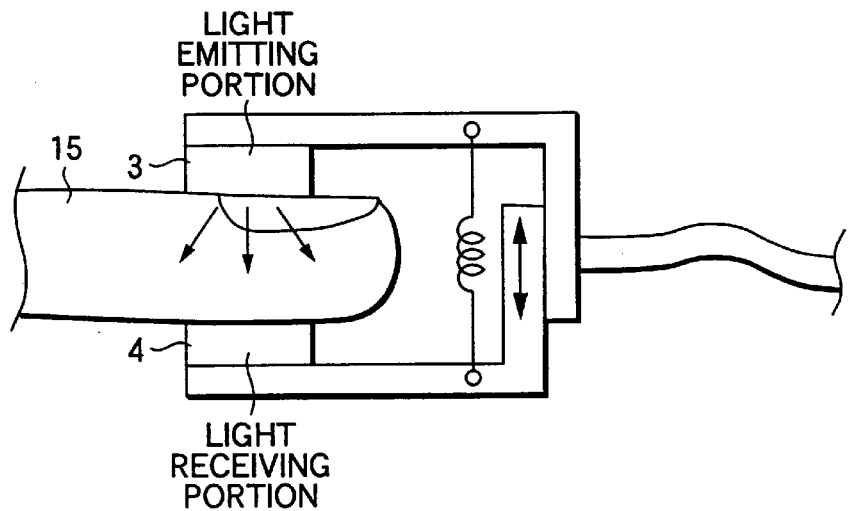
FIG. 11 is a side view showing a third example of the conventional biological sensor.
Figure 12:
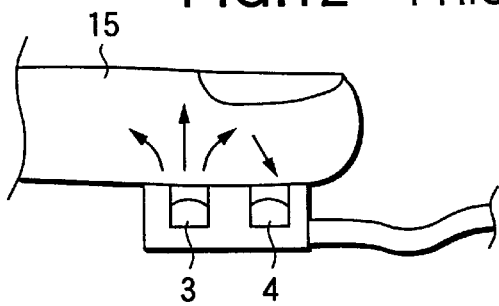
FIG. 12 is a side view showing a fourth example of the conventional biological sensor.
Figure 13:
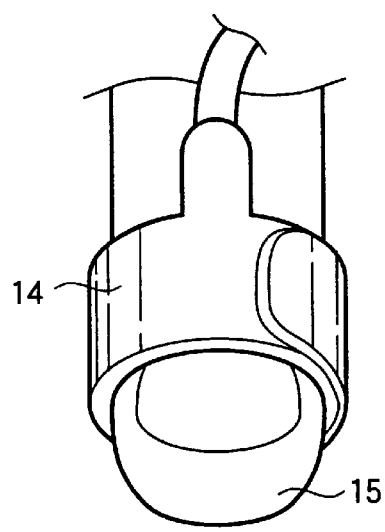
FIG. 13 is a side view showing a fifth example of the conventional biological sensor.
Figure 14:
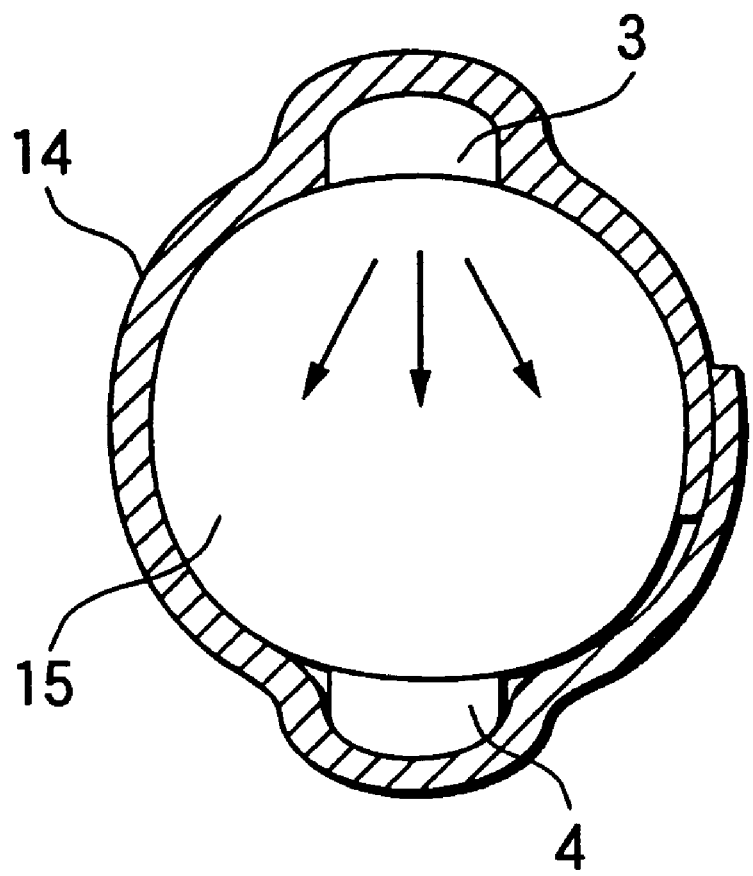
FIG. 14 is a perspective view showing an external view of the FIG. 13 sensor.
Figure 15A:
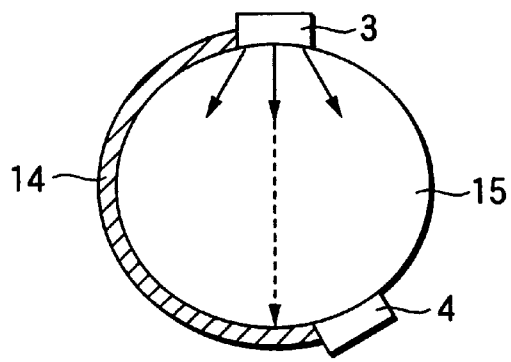
FIGS. 15(a) through 15(c) are diagrams for explaining a first problem of the FIG. 13 sensor.
Figure 15B:
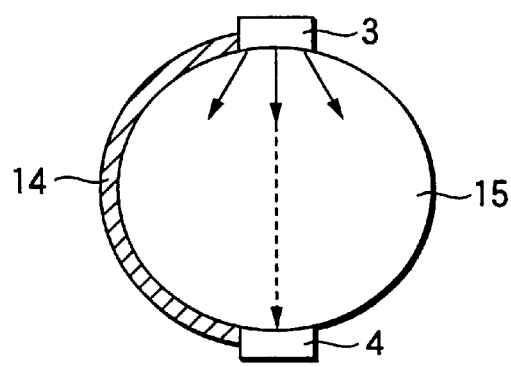
Figure 15C:
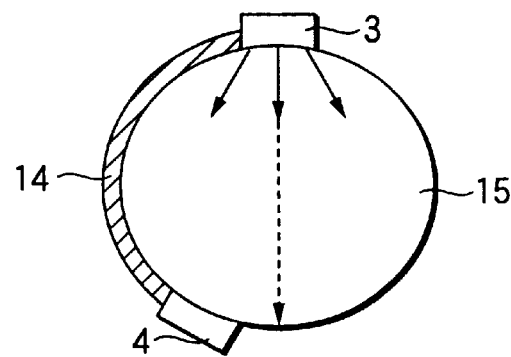
Figure 16:
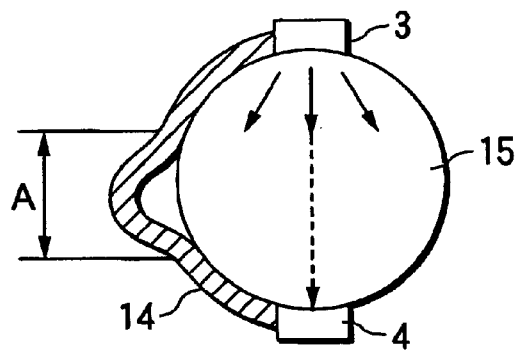
FIG. 16 is a diagram for explaining a second problem of the FIG. 13 sensor.
Figure 17:
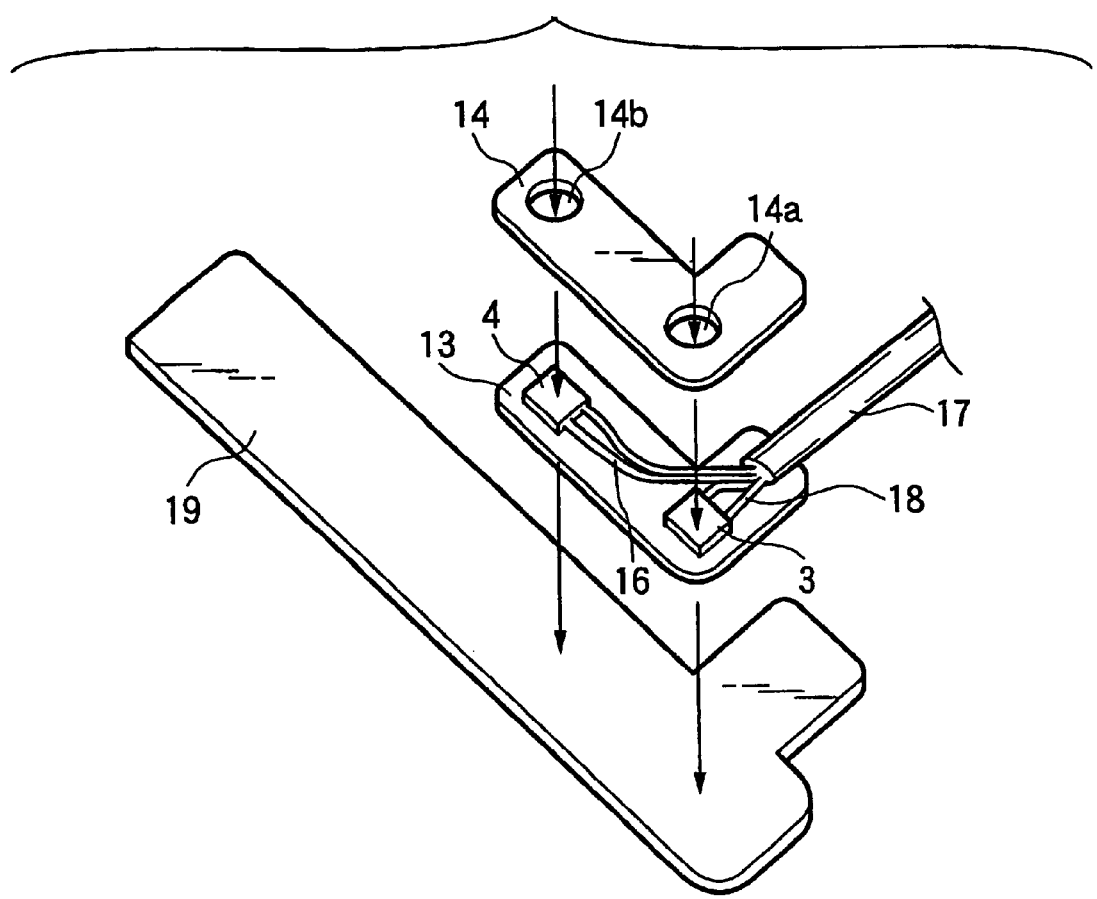
FIG. 17 is an exploded view showing a sixth example of the conventional biological sensor.
Figure 18:
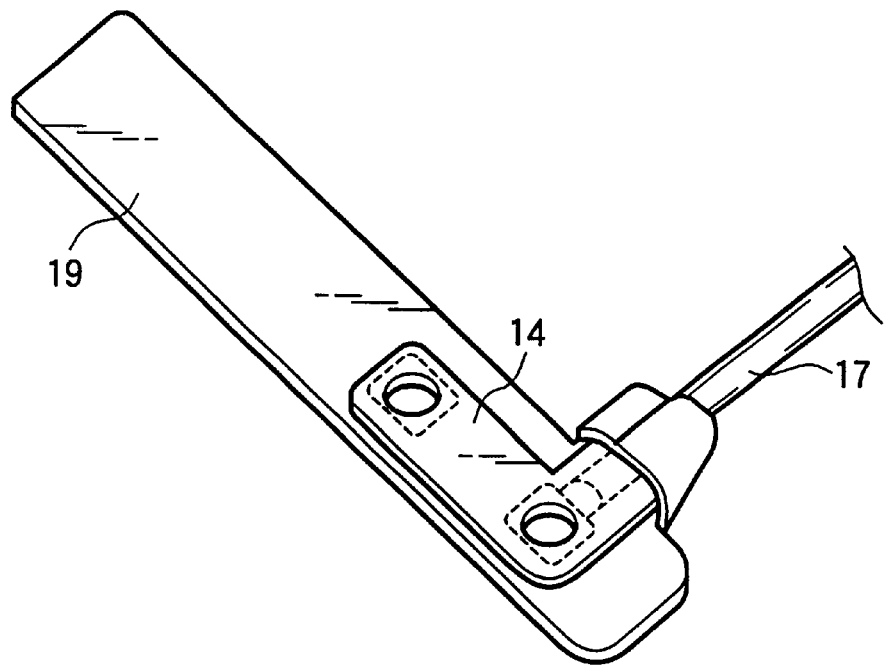
FIG. 18 is a perspective view showing the FIG. 15 example after assembled.
Figure 19:
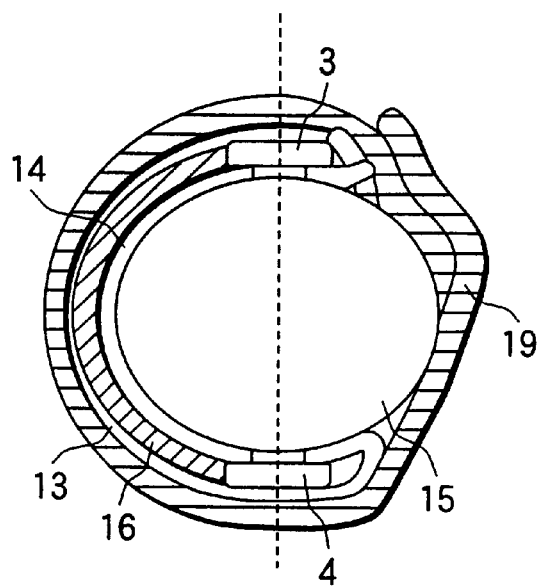
FIG. 19 is a sectional view showing the FIGS. 17 and 18 sensor when it is attached to a finger.
Figure 20:
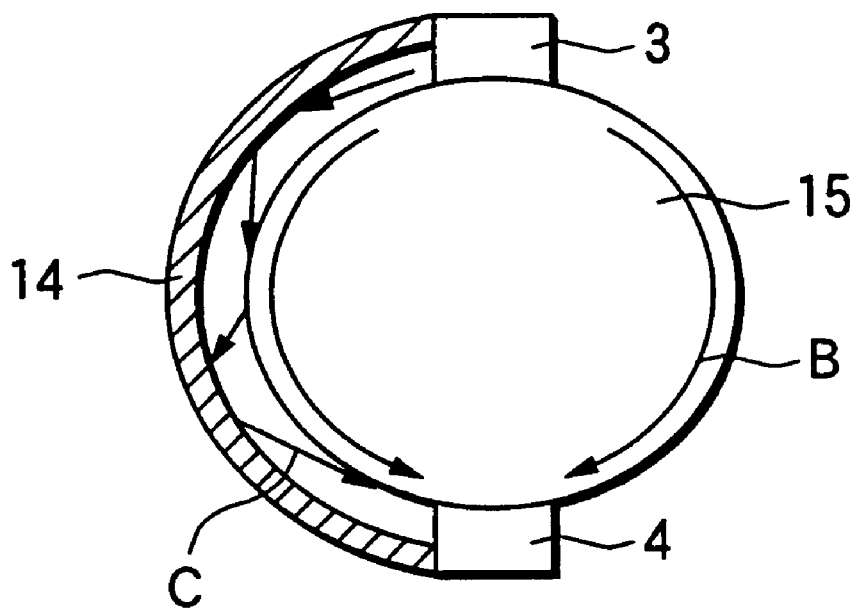
FIG. 20 is a diagram showing leak light in the FIG. 19 sensor.
Figure 21:
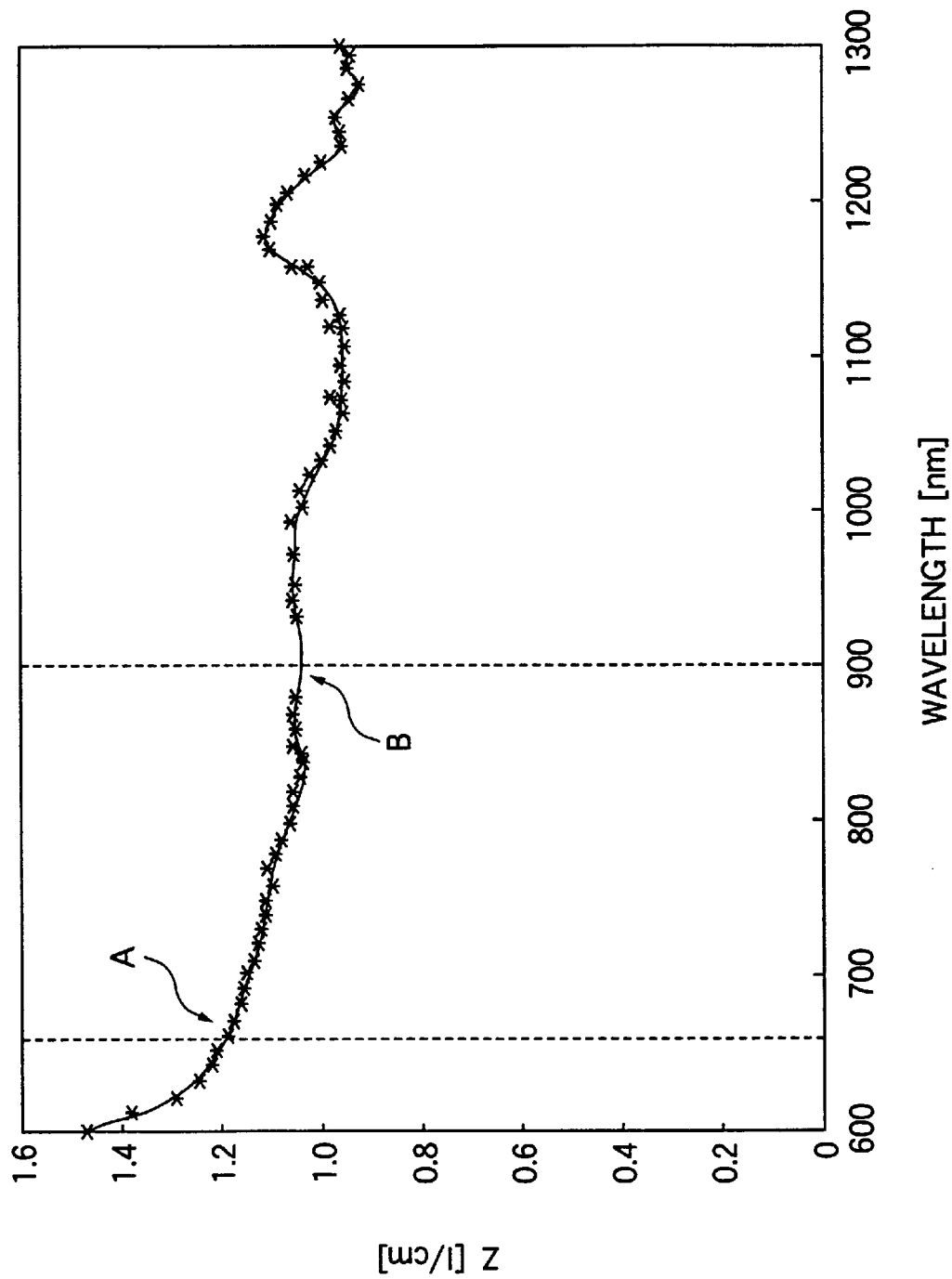
FIG. 21 is a graph showing an attenuation characteristic of fowl from which blood is removed.
Figure 22A:
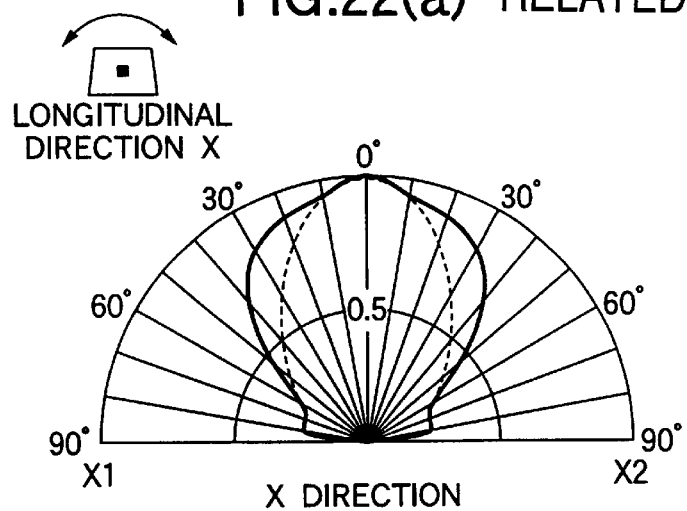
FIGS. 22(a) and 22(b) are graphical representations of a directivity of a light emitting element.
Figure 22B:
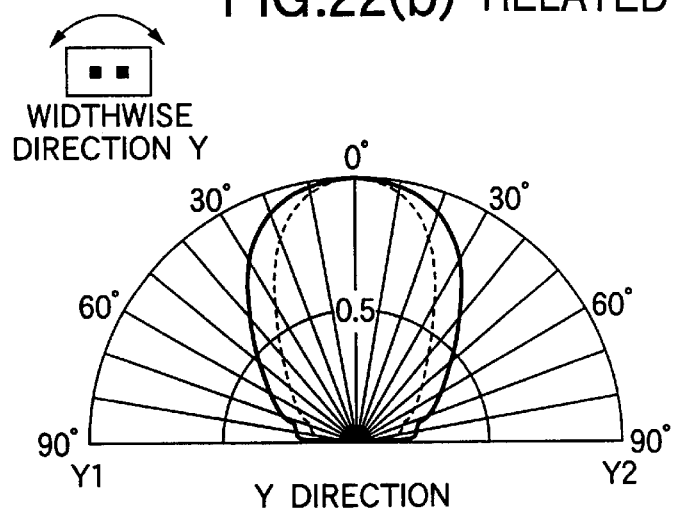
Figure 23:
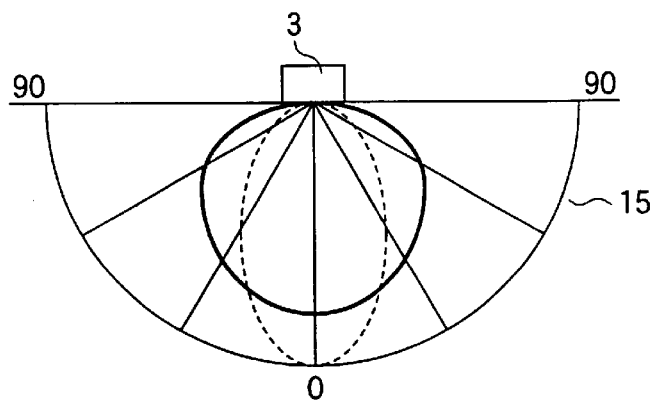
FIG. 23 is a graph showing a scattering difference of lights of different wavelengths, which are irradiated from the light emitting portion into a living body.
Figure 24:
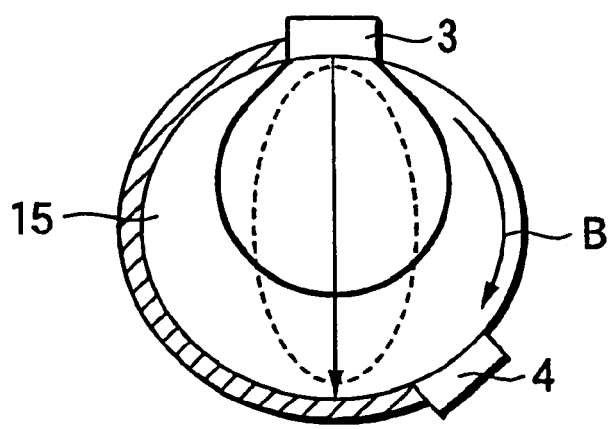
FIG. 24 is an explanatory diagram showing leak lights in the FIG. 15(a) sensor.
Figure 25:
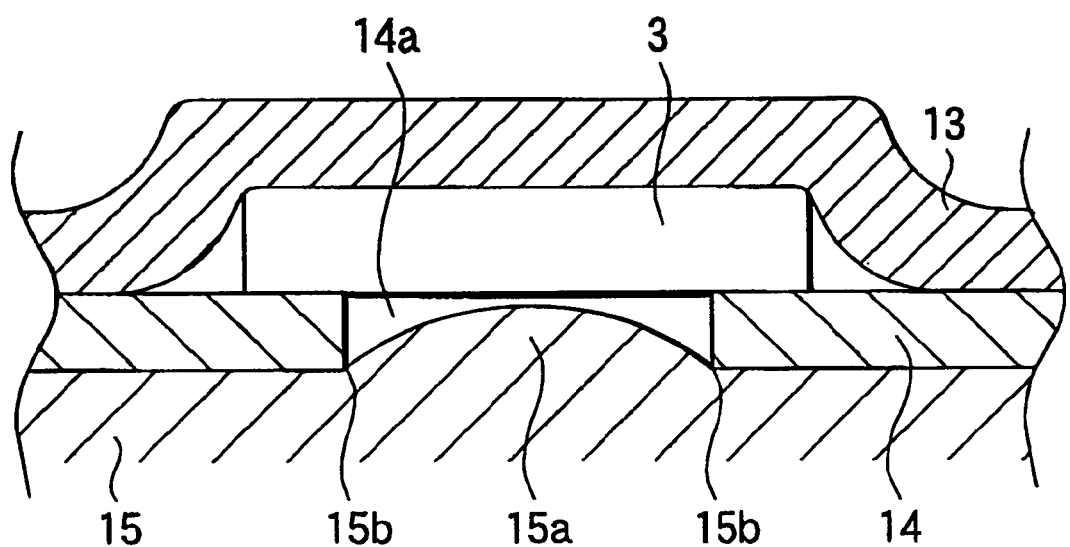
FIG. 25 is a cross sectional view showing a major portion of an example of the attachment of a conventional strip-like sensor to a living body.

An embodiment of a biological sensor according to the present invention will be described with reference to the accompanying drawings. FIGS. 1 and 2 are a cross sectional view and a longitudinal view showing a biological sensor which is an embodiment of the invention, which the sensor is attached to a finger of a living body. FIGS. 3(a) and 3(b) are perspective views showing the obverse side and the reverse side of a light emitting portion in the FIG. 1 sensor before it is attached to the finger. FIGS. 3(c) and 3(d) are perspective views showing the obverse side and the reverse side of a light receiving portion in the FIG. 1 sensor before it is attached to the finger. In those figures, like or equivalent portions are designated by like reference numerals in FIGS. 11 and 12, which show the conventional biological sensor.

In FIGS. 1 and 2, a light emitting portion 3 is firmly interposed between tape members 21 and 25 as separate support structural members, and a light receiving portion 4 is firmly interposed between tape members 23 and 26 as separate support structural members. The tape members 21 and 23 have attaching portions which are flat before those tape members are attached to the finger so as to avoid non-uniform application of pressure onto the attaching portions.

Wiring cables 18 and 16 are connected to the light emitting portion 3 and the light receiving portion 4, respectively. The wiring cable 18 is led out through a space between the tape members 21 and 25, and the wiring cable 16 is led out through a space between the tape members 23 and 26.

A layer coated with adhesive is interposed between the paired tape members 21 and 25, whereby those members are bonded together, and a layer coated with adhesive is also interposed and between the paired tape members 23 and 26, whereby those members are bonded together. Accordingly, those elements of the light emitting portion 3 and the light receiving portion 4, and the cables 18 and 16 are firmly held therebetween. An adhesive layer is provided on a surface of the tape member 21 which is to be in contact with a finger 15. An adhesive layer is also provided on a surface of the tape member 23 which is to be in contact with a finger 15. With those adhesive layers, those elements are firmly attached to a location to be measured.

The probe, as a kind of biological sensors is uniquely provided in that the tape members 21 and 23 are each designed to have a constant transparency. Those features eliminate the need of the spaces as the windows for light transmission formed in the light emitting portion 3 and the light receiving portion 4. Thus, in the embodiment, the windows arrayed on the optical axis of each of the light emitting portion 3 and the light receiving portion 4 are not present. Therefore, a point intersection where the optical axis of the light emitting portion 3 intersects the tape member 21 is denoted as 21a, and a point where the optical axis of the light receiving portion 4 intersects the tape member 23 is denoted as 23a. Those points represent the centers of those elements.

A light emitting piece 22 comprises the light emitting portion 3, wiring cable 18, and tape members 21 and 25. Similarly, a light emitting piece 24 comprises the light receiving portion 4, wiring cable 16, and tape members 23 and 26. Those pieces are configured as shown in FIG. 3. The light emitting piece 22 is symmetrical in shape with respect to a location at which the light emitting portion 3 is located. The light emitting piece 24 is likewise symmetrical in shape with respect to a location at which the light receiving portion 4 is located. The light emitting piece 22 is provided with wings 25a extending to both sides. The light emitting piece 24 is provided with wings 26a extending to both sides. To protect the adhesive layer of the tape member 21, a surface of the light emitting piece 22, which is to be applied to the finger, is covered with a release paper before it is used. A surface of the light emitting piece 24, which is to be applied to the finger, is also covered with a release paper before it is used, for the same purpose. A finger-shaped mark is printed at the central portion of the light emitting piece 22, while being oriented in the probe attaching direction. A finger-shaped mark is also printed at the same location of the light emitting piece 24 and oriented in the same direction. The print of the marks makes it easy to attach the probe to a correct location of the living body.

Figure 4A:
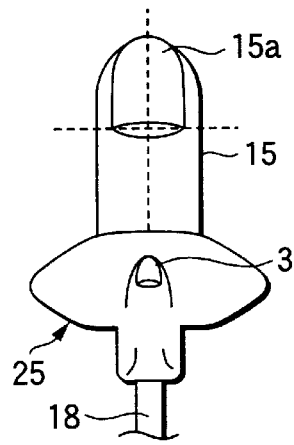
FIGS. 4(a) to (e) are explanatory diagrams showing a sequence of steps for attaching the biological sensor shown in FIGS. 1 and 2.
Figure 4B:
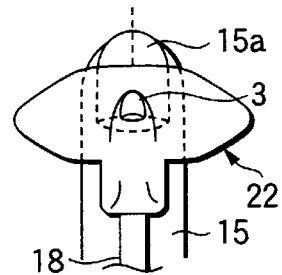

A procedure to attach a thus constructed probe of the embodiment to a finger 15 will be described with reference to FIG. 4. An operator, as shown in FIG. 3(b), peels a release paper 27 from the light emitting piece 22, and arranges the light emitting piece such that as shown in FIGS. 4(a) and 4(b), the center of the light emitting portion 3 is positioned at the lunula part near a nail line of a nail 15a of the finger 15, and fixed there firmly. At this time, the tape member 25 of the light emitting piece 22 is distinctly bulged out in the form of the element of the light emitting portion 3.

This step of the attaching procedure is to manually set the center 21a of the light emitting element at the target location of the living body. This attaching operation of the probe is much easily performed when comparing with the attaching operation of the conventional product in which a display position is printed or indicated in any of other ways. Since it is printed, an error that is present between the element-center indicating position and the actual element position is completely eliminated. As a result, the preciseness is also improved.

Figure 4C:
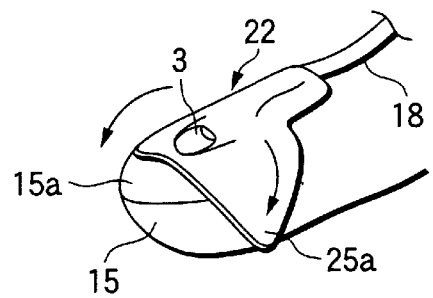
Figure 4D:
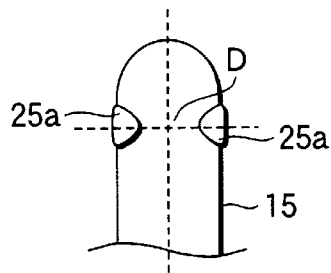

Then, as shown in FIG. 4(c), the operator firmly fixes both the wings 25a of the attached light emitting piece 22 onto the finger 15. FIG. 4(d) is a view showing the probe thus attached, when viewed from the inner side of the tip of the finger 15. The wings 25a is wound reaching both sides of the finger tip. A center line between both sides of the wings 25a is coincident with the optical axis D.

Figure 4E:
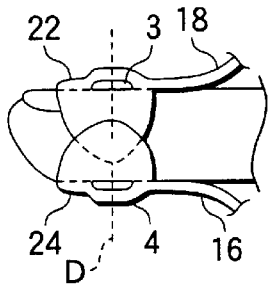

Next, the operator attaches the light emitting piece 24 to the finger tip. As in the attaching operation of the light emitting piece 22, the operator peels a release paper 28 that is stuck to the finger attaching side, from the light emitting piece 24. And the operator fixes the light emitting piece 24 to the finger such that the light receiving portion 4 of the light emitting piece 24 is superimposed on the optical axis D of the already attached light emitting piece 22 shown in FIG. 4(d). This state is shown in FIG. 4(e). As a matter of course, the tape member 26 is distinctly bulged out in the form of the element of the light receiving portion 4. Accordingly, its positioning is easy.

Figure 5A:
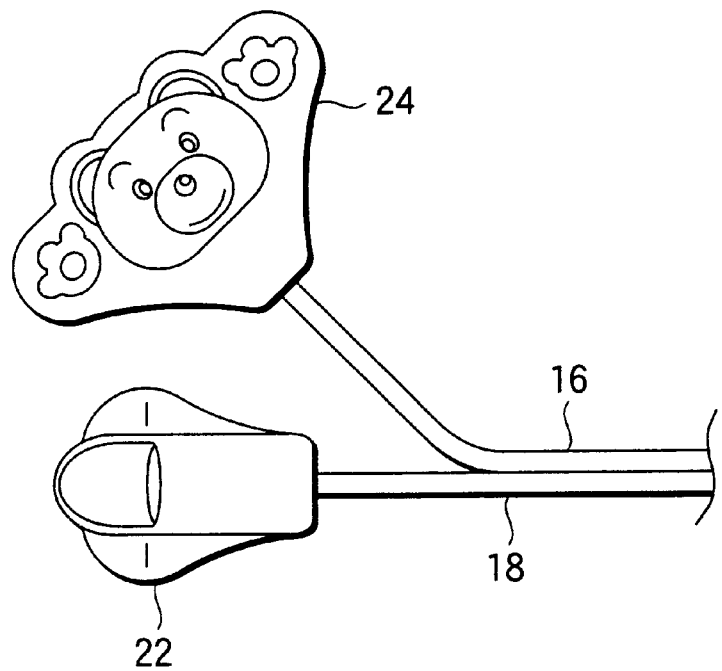
FIGS. 5(a) and (b) are perspective views showing a biological sensor which is a second embodiment of the invention.
Figure 5B:
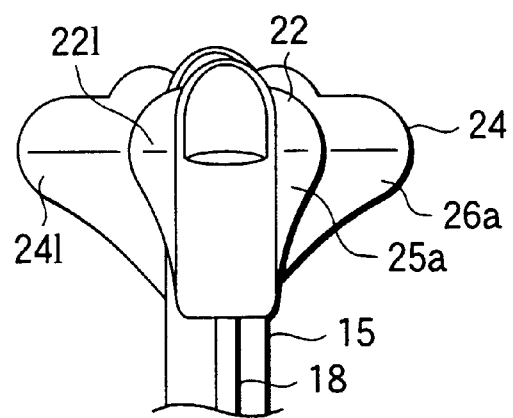

A second embodiment of the present invention is illustrated in FIGS. 5(a) and 5(b). In those figures, like or equivalent portions are designated by like reference numerals in FIGS. 1 to 4. In the second embodiment, an illustration of an animal (bear in the embodiment) is printed on a tape member 26 of the light receiving piece 24 in order to clearly show that the sensor is used for the pediatric diagnosis. As in the first embodiment, the light emitting piece 22 is symmetrically configured with respect to a prolongation of the wiring cable 16. The light receiving piece 24 is also symmetrically configured with respect to a prolongation of the wiring cable 18. A reference line 22L, which is referred to when the sensor is attached to the finger, is printed on the light emitting piece 22. A reference line 24L, which is referred to when the sensor is attached to the finger, is printed on the light emitting piece 24. The reference line 24L may be printed on the tape member 23. If the tape member 23 is transparent, it may be printed on the tape member 26. The reference lines 22L and 24L are perpendicular to the finger when the sensor is attached to the finger, and extend to the vertices of the wings 25a and 26a.

To attach the sensor to the finger, as shown in FIG. 5(b), the light emitting piece 22 is brought into contact with the finger 15 in a state that the center of the light emitting portion 3 is positioned at a lunula portion of a nail face of the finger 15. Then, the light receiving piece 24 is brought into contact with the opposite side of the finger such that the reference line 24L of the light receiving piece 24 and the reference line 22L line up straight as viewed from the finger nail side. In this state, the vertices of the wing pairs 25a and 26a line up straight. Further, the light emitting portion 3 and the light receiving portion 4 are configured within those small pieces in a state that the optical axes of those portions 3 and 4 are coincident with each other. Then, the paired wings are applied to the finger in the order of the wings 25a and the wings 26a. Since the reference line 22L is formed on the light emitting piece 22 and the reference line 24L is formed on the light receiving piece 24, the optical axis of the light emitting portion 3 may be coincident with that of the light receiving portion 4 more reliably and easily. The same useful effects will be produced when the size relation between the wings pairs 25a and 26a is reversed and the reference lines are printed on the reverse sides of the small pieces.

Figure 6A:
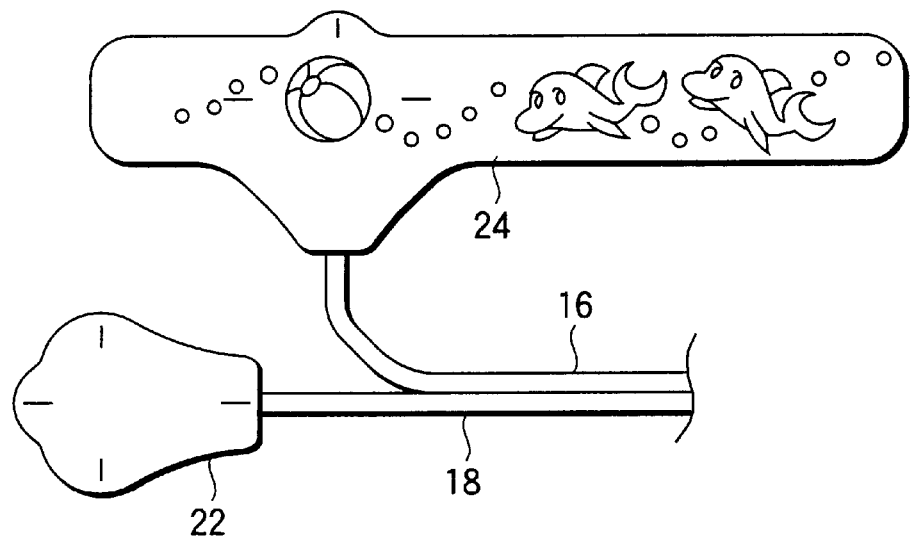
FIGS. 6(a) and (b) are perspective views showing a biological sensor which is a second embodiment of the invention.
Figure 6B:
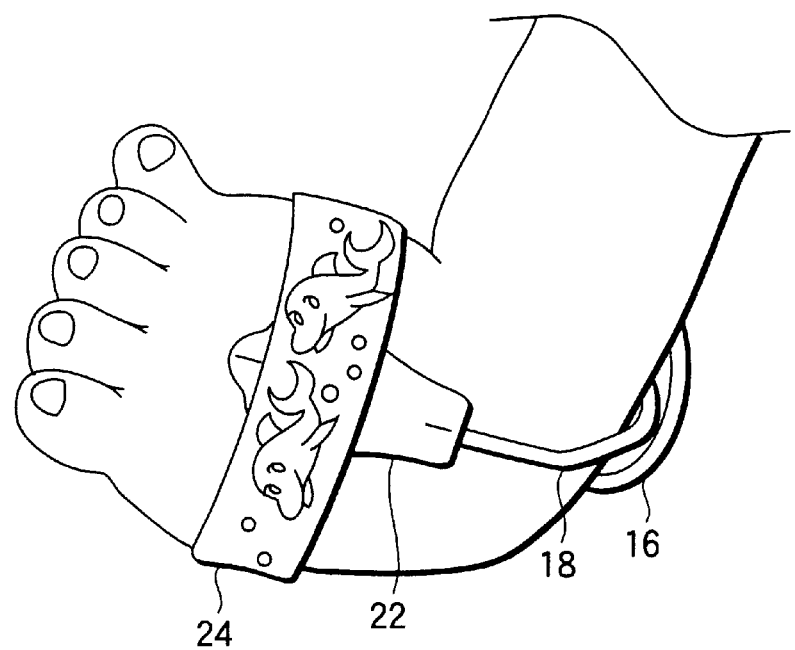
Figure 7:
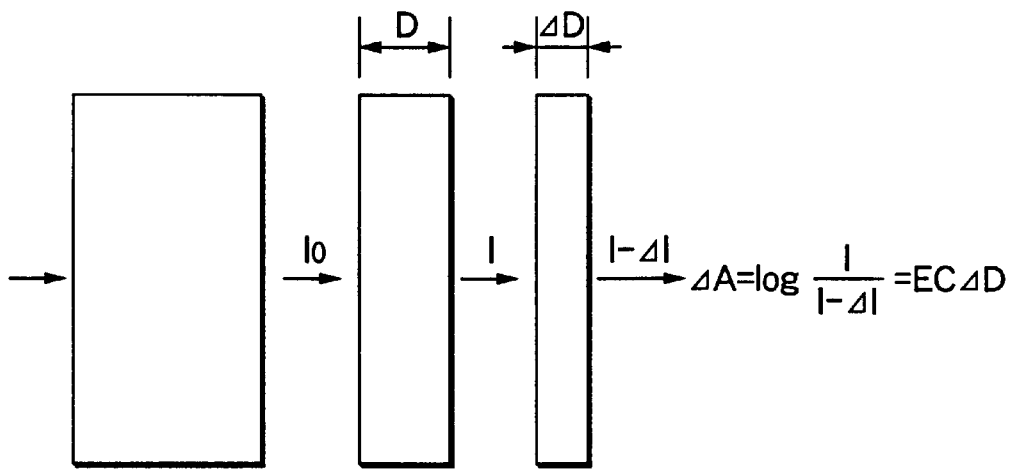
FIG. 7 is a block diagram showing the principle of a pulse oximeter.
Figure 8:
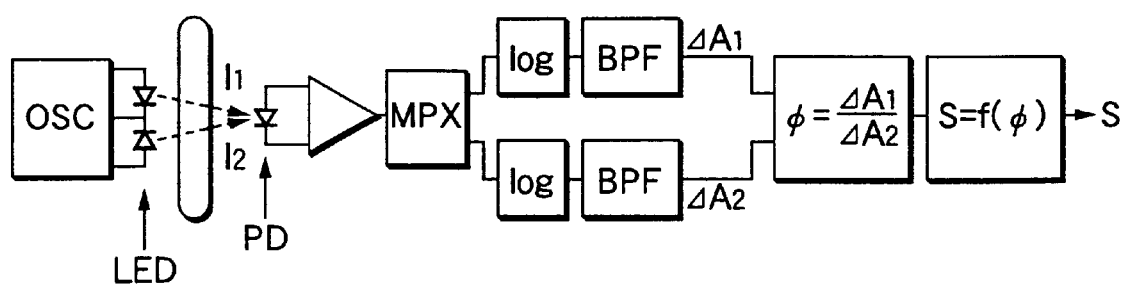
FIG. 8 shows in block and schematic form a basic construction of an example of a pulse oximeter.
Figure 9:
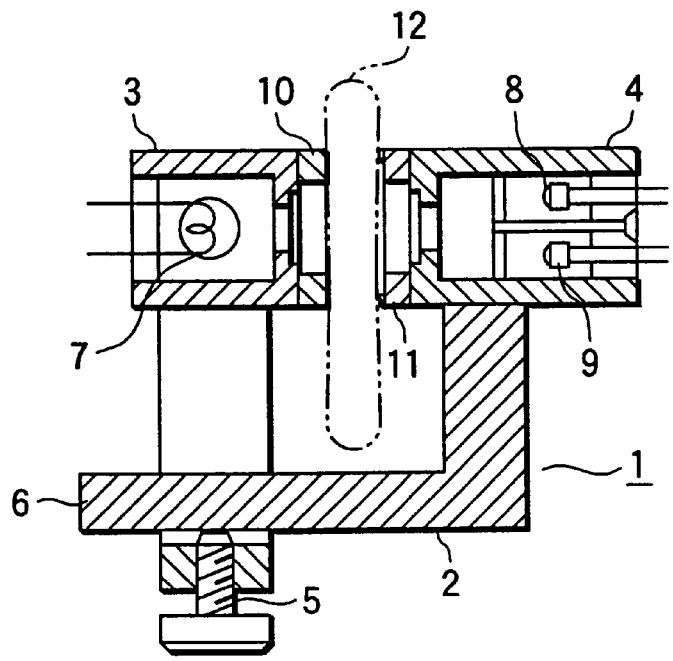
FIG. 9 is a cross sectional view showing a construction of a first example of a conventional biological sensor.
Figure 10:
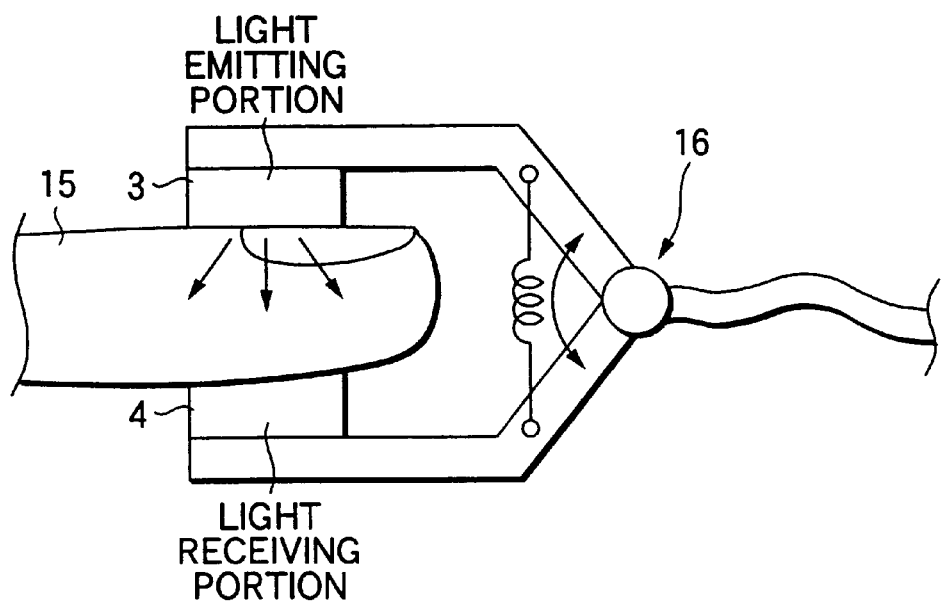
FIG. 10 is a side view showing a second example of the conventional biological sensor.

A third embodiment of a sensor according to the present invention is shown in FIGS. 6(a) and 6(b). In those figures, like or equivalent portions are designated by like reference numerals in FIGS. 1 to 5. The sensor of this embodiment is used for a neonate's foot. Animals (dolphins), which are different from the animal illustrated on the light emitting piece in the second embodiment, are illustrated on a light receiving piece in order to clearly show that the sensor is used for neonate. The light emitting piece 22 is configured to be symmetrical with respect to the wiring cable. However, the light receiving piece 24 is shaped like L so that it is completely wound around the foot of the neonate.

To attach the sensor of the embodiment to the foot of the neonate, the light emitting piece 22 is put on the instep or therearound. The light emitting portion 3 and the light receiving portion 4 are arranged so that the optical axes of them are coincident with each other. Then, the long side of the L-shaped light receiving piece 24 is wound around the foot as shown in FIG. 6(b). If required, the light emitting piece 22 may be shaped like L instead of the light receiving piece 24. In this case, the light receiving piece 24 is configured to be symmetrical with respect to the wiring cable.

In the embodiment, the light emitting portion 3 and the light receiving portion 4 are formed as separate pieces, and those separate pieces are stuck to the finger 15. Therefore, the optical axes of the light emitting portion 3 and the light receiving portion 4 can be made coincident with each other, independently of the thickness of the finger 15 as the object to which the probe is attached. Accordingly, the probe of the invention is free from the measurement error as described in detail in the background art discussion.

The probe of the invention has the following advantages. The covers 21, 22, 23 and 24 as the support structural members are reduced in size. It never happens that the covers erroneously stick to each other. In this sense, the operability in attaching the covers is improved. Accordingly, the attaching operation of the probe is easy and exact. The wiring cables 18 and 16 connected to the light emitting portion 3 and the light receiving portion 4 may be led out from locations where the fixing by sticking is not hindered, and there is eliminated the lessening of partial flexibility of the covers and the tape members. As a result, the operability in sticking the members is improved, and any additional load is not imposed on the probe-attaching location of the patient. Also when a situation that the measuring location must be changed to another occurs, and the sticking of the tape members starts again, the sticking operation is more efficiently performed when comparing with that using the conventional strip-like member since the light emitting portion 3 and the light receiving portion 4 may separately be attached to and detached from the patient.

As seen from the foregoing description, the light emitting portion and the light receiving portion are formed as separate pieces, and those pieces are attached to opposed skin surfaces of a living body in a state that the optical axes of them are coincident with each other. Therefore, a concentration of a material in a living body can be non-invasively and exactly measured independently of a thickness of a probe attaching portion of a living body.

Further, the light emitting portion and the light receiving portion are fixed to the separate support structural members, respectively. Accordingly, the support structural members may be reduced in size, and the operability in attaching the probe is improved.

The probe of the invention uses the transparent tape members for the tape members to be stuck to the living body. Therefore, there is no need of the light measuring windows of the elements, which are conventionally formed in the probe portions which will come in contact with a living body. Therefore, no steps are formed at the window contoured edges by the tape thickness. Accordingly, the invasion to the patient's skin at the probe attaching location is lessened.

The support structural members are each symmetrically configured with respect to a line on which said light emitting portion or said light receiving portion lies. With this feature, the operator can easily position the light emitting portion and the light receiving portion at the target locations to the skin surface of the living body from the shapes of the support structural members. Further, in the probe, the support structural members are each provided with the wings. With the provision of the wings, the light emitting portion and the light receiving portion may easily be disposed oppositely.

What is claimed is:

1. A biological sensor for non-invasively measuring a concentration of a material in a living body by detachably attaching said biological sensor to a skin surface of the living body, comprising:

a light emitting portion and a light receiving portion for detecting lights emitted from said light emitting portion and transmitted through the living body, said light emitting portion and said light receiving portion being attached to the opposed locations of a skin surface of the living body, said light emitting portion and said light receiving portion being fixedly secured to separate means for attaching to the living body.

2. The biological sensor according to claim 1, wherein said means for attaching to the living body include pairs of tape members which interpose respectively said light emitting portion and said light receiving portion, and said tape members covering respectively a light emitting surface of said light emitting portion and a light receiving surface of said light receiving portion are transparent.

3. The biological sensor according to claim 1, wherein at least one of said means for attaching to the living body is symmetrically configured with respect to a line on which one of said light emitting portion and said light receiving portion lies.

4. The biological sensor according to claim 2, wherein at least one of said means for attaching to the living body is symmetrically configured with respect to a line on which one of said light emitting portion and said light receiving portion lies, and said means for attaching to the living body includes wings extending to both sides.

5. The biological sensor according to claim 2, wherein said means for attaching to the living body are each symmetrically configured with respect to a line on which said light emitting portion and said light receiving portion lies respectively, and each said means for attaching to the living body includes wings extending to both sides.

6. The biological sensor according to claim 1, wherein at least one of said means for attaching to the living body has a mark being oriented in a direction in which said means for attaching to the living body is attached to said living body location.

7. The biological sensor according to claim 1, wherein each of means for attaching to the living body has a reference line, which is referred to when said light emitting portion and said light receiving portion are attached in a state that the optical axes of said light emitting portion and said light receiving portion are coincident with each other.

8. The biological sensor according to claim 1, wherein one of said means for attaching to the living body has a mark indicating that said biological sensor is used for one of a neonate or a pediatric patient.

9. A biological sensor for non-invasively measuring a concentration of a material in a living body, comprising:

a light emitter, provided with a light emitting face;

a light receiver, provided with a light receiving face;

a first support member, which supports the light emitter, the first support member adapted to be attached on a first portion of a skin surface of the living body; and a second support member, which supports the light receiver, the second support member adapted to be attached on a second portion of the skin surface of the living body which opposes to the first portion, so that light emitted from the light emitter and transmitted through the living body is received by the light receiver, wherein the first support member and the second support member are provided separately, but are attached to the skin surface of the living body so as to be superposed with each other at least partly.

10. The biological sensor according to claim 9, wherein:

the first support member includes a first, transparent member attached on the light emitting face and a second member which sandwiches the light emitter with the first member; and the second support member includes a third, transparent member attached on the light receiving face and a fourth member which sandwiches the light receiver with the third member.

11. The biological sensor according to claim 9, wherein the first support member has a shape having linear symmetry, so that the light emitter is placed on a center line of the linear symmetry.

12. The biological sensor according to claim 11, wherein the first support member has wing portions, so that a line connecting both ends of the wing portions crosses a portion where the light emitter is placed.

13. The biological sensor according to claim 12, wherein at least one of the center line and the line connecting both ends of the wing portions is indicated on the first support member.

14. The biological sensor according to claim 9, wherein the second support member has a shape having linear symmetry, so that the light receiver is placed on a center line of the linear symmetry.

15. The biological sensor according to claim 14, wherein the second support member has wing portions, so that a line connecting both ends of the wing portions crosses a portion where the light receiver is placed.

16. The biological sensor according to claim 15, wherein at least one of the center line and the line connecting both ends of the wing portions is indicated on the second support member.

17. The biological sensor according to claim 9, wherein the first support member supports the light emitter such that an outline shape of the light emitter is ascertained.

18. The biological sensor according to claim 9, wherein the second support member supports the light receiver such that an outline shape of the light receiver is ascertained.

* * * * *